United States Patent [19]

Craig et al.

[11] 4,208,586
[45] Jun. 17, 1980

[54] POWER ASSIST FLUOROSCOPIC TABLE

[75] Inventors: James R. Craig, Glenview; Steven F. Nerge, Elgin, both of Ill.

[73] Assignee: Raytheon Company, Lexington, Mass.

[21] Appl. No.: 962,727

[22] Filed: Nov. 21, 1978

[51] Int. Cl.² .................................................. A61B 6/00
[52] U.S. Cl. .................................. 250/447; 250/445 R
[58] Field of Search ........................... 250/445 R, 447

[56] References Cited

U.S. PATENT DOCUMENTS 2,822,477  2/1958  Kizaur .................................... 250/447

Primary Examiner—Alfred E. Smith
Assistant Examiner—T. N. Grigsby
Attorney, Agent, or Firm—Richard M. Sharkansky; Joseph D. Pannone

[57] ABSTRACT

A fluoroscopic table having an electrically operated motor for moving the heavy fluoroscopic staging in a direction longitudinally of the table, the motor being controlled by a drive circuit which produces a constant output torque at the motor shaft which is of a predetermined value slightly less than the effort necessary to automatically initiate motion of the staging whereby an operator may apply only a slight amount of effort to cause such motion and will retain a natural "feel" of control.

10 Claims, 5 Drawing Figures

POWER ASSIST FLUOROSCOPIC TABLE

BACKGROUND OF THE INVENTION

Fluoroscopic tables are commonly used for supporting a patient in a position to be irradiated by a beam of X-rays or other selected radiation. One conventional type of X-ray apparatus for diagnostic purposes includes a table having a top upon which the patient is positioned during the diagnostic procedure, and an X-ray source which is located above the patient and which directs X-rays downwardly through the patient and table top to a bucky which is carried by the table beneath the patient. The bucky includes an X-ray film cassette or carrier that positions the plane of the film substantially parallel to the table top. Such prior art apparatus is disclosed in U.S. Pat. No. 3,967,126 issued on June 29, 1976 to George W. Otto, Jr.

Later developments in the field of X-ray fluoroscopy included the production of X-ray image intensifiers which replace the bucky when it is desired to obtain immediate fluoroscopic viewing of an irradiated area. The image intensifier is an electron imaging device which converts an X-ray image first to an electron image and then to a visible image. Thus, when an X-ray beam is directed through a patient, there is formed an X-ray image which is directed onto the face of the image intensifier which immediately forms a visible image which may be viewed by the doctor or technician without waiting for development of films. Filming or television reproduction of the visible images produced by the image intensifier are also possible by known techniques.

One type of prior art system utilizing an X-ray image intensifier is disclosed in U.S. Pat. No. 3,912,936, issued Oct. 14, 1975 to Cunninghame et al.

Image intensifiers and their associated optical or reproducing apparatus make up a fluoroscopic staging which is extremely bulky and the combined weights of the staging components may approach as much as 450 to 500 pounds, for example. When such fluoroscopic staging is used, the X-ray generator is placed beneath the table top and the staging is located above the patient. The staging and X-ray generator must always be aligned and, therefore, they are located at opposite ends of a tower which extends vertically from the back of the table and is movable in a direction longitudinally or parallel to the table top.

Since great physical effort is required when scanning a patient during a fluoroscopic examination, a motor drive is conventionally used for powering the system to simultaneously move the staging and generator so as to position the apparatus in desired position with respect to the area of the patient's body to be irradiated. Numerous power drives or assists have been designed to minimize the effort required by a fluoroscopist. It has been found advisible to keep the manual effort for this purpose to between two and six pounds, for example, in any direction of scanning. However, the problem becomes even more complicated when the system components must be moved vertically such as when the table is in an upright position. Also, it is very important to the fluoroscopist that he maintain complete control of all motions of the apparatus and that the power assist not overdrive.

A conventional motor drive system employing constant voltage or constant power drive will produce wide variations in assist effort depending on load velocity and variations in load due to high friction spots, slight misalignments, etc. This negates the feeling of complete control by the operator.

SUMMARY OF THE INVENTION

The present invention overcomes the above and other objections to prior art apparatus of the described character by the provision of a fluoroscopic table having its staging and generator powered by a motor under the control of a unique electronically controlled and powered drive circuit which operates in such a manner as to produce a constant current to the motor armature. In the present system, the motor voltage is caused to vary inversely with the speed of the motor so that the output torque at the motor shaft is a preset constant, regardless of the motor speed.

Applied as a force, for example, to assist the longitudinal travel of the staging and generator, the torque can be preadjusted to apply a constant force somewhat less than total effort necessary to overcome the friction load. The balance of the effort, which may be adjusted to be between two and six pounds, for example, is exerted by the operator, thus allowing him to maintain a natural feel of control.

As an example, a power drive may be achieved by a series would DC motor to move a load which may require about 500 lbs., for example, of horizontal force to get it in motion. According to this invention, the DC motor is controlled from a controlled current source, and when the current is slowly turned up and the 500 lb. effort point is met the load will start to move but will not accelerate, as opposed to the prior art voltage controlled motor where when the voltage is increased slowly the load will not move until the voltage level is reached which creates a torque sufficient to overcome the 500 lb. load, and when the load starts to move it will also begin to accelerate.

With the presently described system, if the current is reduced to about the 475 lb. point, for example, the load can be manually pushed with very little effort, and its position along its linear path can be located with precision.

BRIEF DESCRIPTION OF THE DRAWINGS

The above and other advantages of the invention will become apparent from the following description taken in connection with the accompanying drawings, wherein.

DESCRIPTION OF THE PREFERRED EMBODIMENTS

Figure 1:
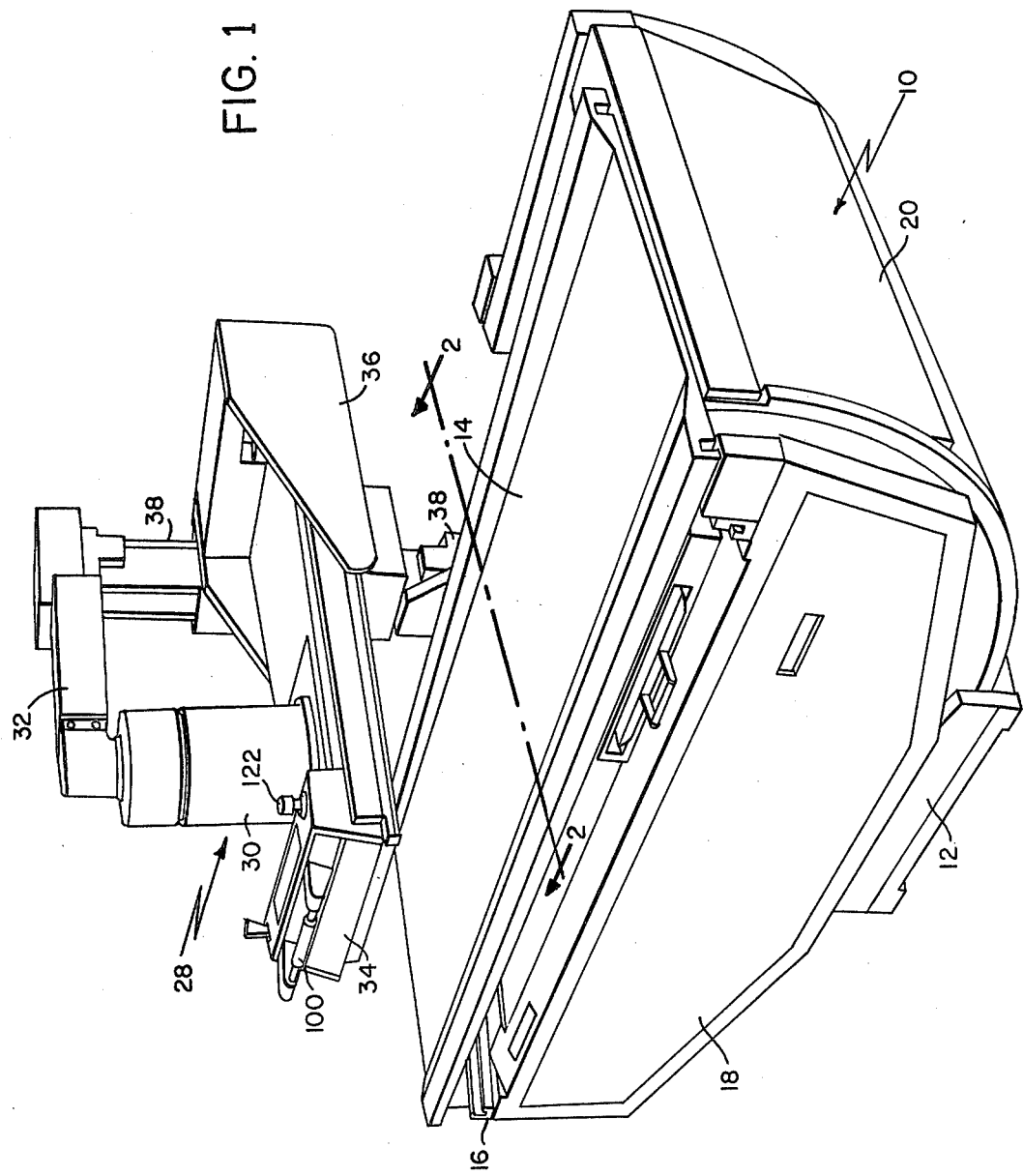
FIG. 1 is an isometric view of a radiographic or fluoroscopic table with which the invention is used.

Referring more particularly to the drawings, wherein like characters of reference designate like parts throughout the several views, there is shown in FIG. 1 a fluoroscopic table 10 mounted on a base or pedestal 12 and having a top 14 on which a patient lies. The top 14 is suitably mounted on a frame or carriage 16 for planar movement in any direction, the means for accomplishing such movement not comprising a part of this invention. The table has a front panel 18 and end panels 20 which enclose the operative mechanisms within the structure.

Figure 2:
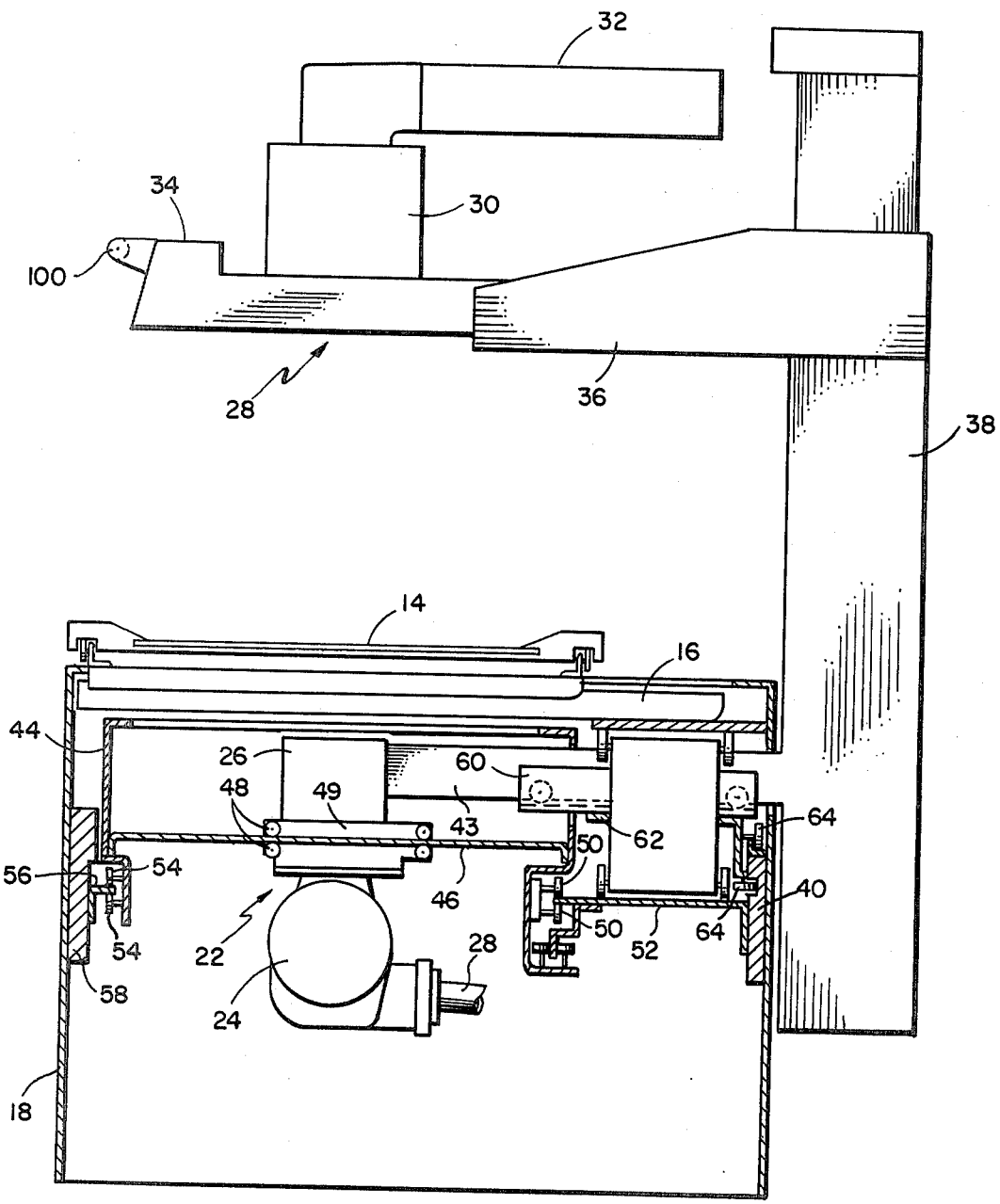
FIG. 2 is a vertical sectional view taken along line 2—2 of FIG. 1 looking in the direction of the arrows.

As seen in FIG. 2, a radiation source assembly 22 is located within the table and includes an X-ray generator 24 and an X-ray collimator 26.

The X-ray tube or generator 24 is connected by cables 28 to a suitable power source and is adapted to generate X-radiation which passes upwardly through the collimator 26 and through the table top 14 to a patient lying on the top. The X-ray beam passing through the patient will fall onto an X-ray image intensifier 30 which, together with additional equipment such as optical devices 32 and spot film devices 34, is mounted by a suitable support 36 at the upper end of a tower 38. Tower 38 extends vertically from the rear of the table as shown in FIG. 2, and the receptor assembly 28 is vertically movable on the tower 38 toward and away from the source assembly 22 as will be described.

The lower end of the tower is movably mounted on the rear of the table and, as shown in FIG. 2, is secured to a longitudinally extending frame member 40. The tower is adapted to move longitudinally of the table on frame member 40 as by upper and lower rollers 42.

The tower is connected to the source assembly 22 by a bar 43 one end of which is slidable within a rigid frame 44 within which the source assembly is positioned. A pair of transversely extending plates 46 serve as tracks engaged by rollers 48 carried by a support collar 49 or the like which is secured about the collimator 26. Thus, the source assembly is movable on the tracks 48 in a direction laterally of the table.

To permit longitudinal movement of the source assembly 22, the frame 44 is mounted as by rollers 50, at the back side of the structure, which engage a longitudinally extending plate 52 fixed to frame member 40. At the front of the structure, rollers 54 on the frame 44 engage a track or angle bar 56 which extends longitudinally of the table frame member 58. Thus, the source assembly 22 may be moved longitudinally of the table simultaneously with corresponding longitudinal movement of the tower 38. In this way the source and receptor assemblies 22 and 28 are maintained in vertical alignment at all longitudinal positions of the assemblies.

The receptor assembly 28 is fixed to the tower 38 as described and may be adjusted laterally or transversely of the table by manual manipulation on the part of the operator. Thus, the source assembly 22 will also be simultaneously transversely adjusted in order to constantly maintain the two assemblies in aligned relations. In order to achieve simultaneous and corresponding movement of the source assembly 22 any suitable means may be employed such as the structure illustrated in FIG. 2 wherein the bar 43 is shown as supported and laterally movable in a channel member 60 which is mounted as by a bracket 62 and rollers 64 on frame member 40. Thus, lateral movement of receptor assembly 28 manually by the operator will cause corresponding movement of the tower 38 toward or away from the back of the table. Since bar 43 is connected to the frame 44, such movement will cause corresponding movement of the source assembly 22.

Figure 3:
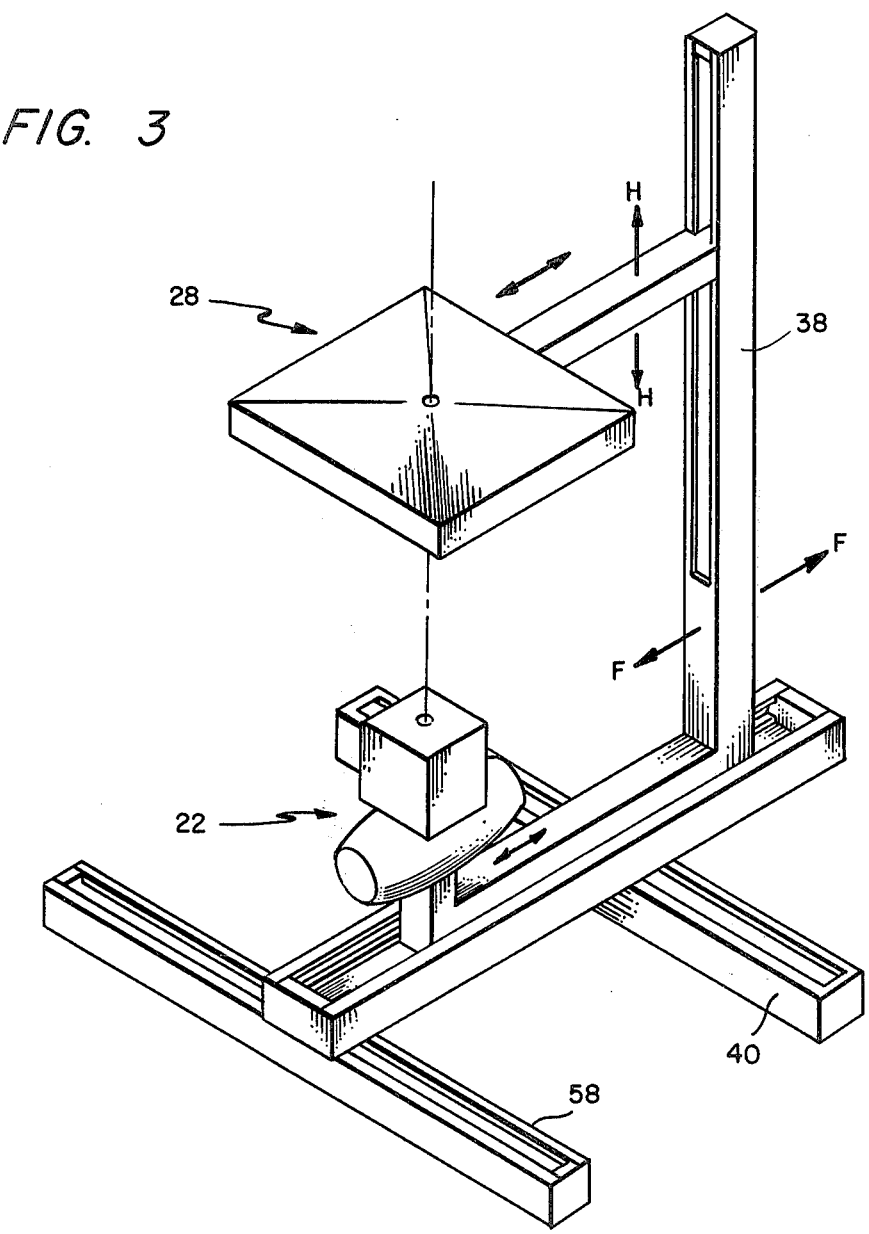
FIG. 3 is a diagram illustrating the various adjustments or motions of the receptor and source assemblies.

A better understanding of the various adjustments achieved by the described structures may be had from the diagram in FIG. 3. Here it will be seen that the receptor assembly 28 is itself adjustable transversely of the table together and simultaneously with corresponding transverse movement of the source assembly 22. This is accomplished by virtue of the fact that both assemblies 22 and 28 are fixed to tower 38. Thus, upon movement of tower 38 in the direction of arrows F-F, both assemblies will simultaneously move transversely of the table but will maintain their aligned relation.

The receptor assembly 28 is also individually movable vertically toward and away from the source assembly 22 in the direction of arrows H-H, as will be described. Further, the entire staging, receptor assembly 28, tower 38, and source assembly 22 are movable as a unit longitudinally of the table on tracks or frame members 40 and 58.

Figure 4:
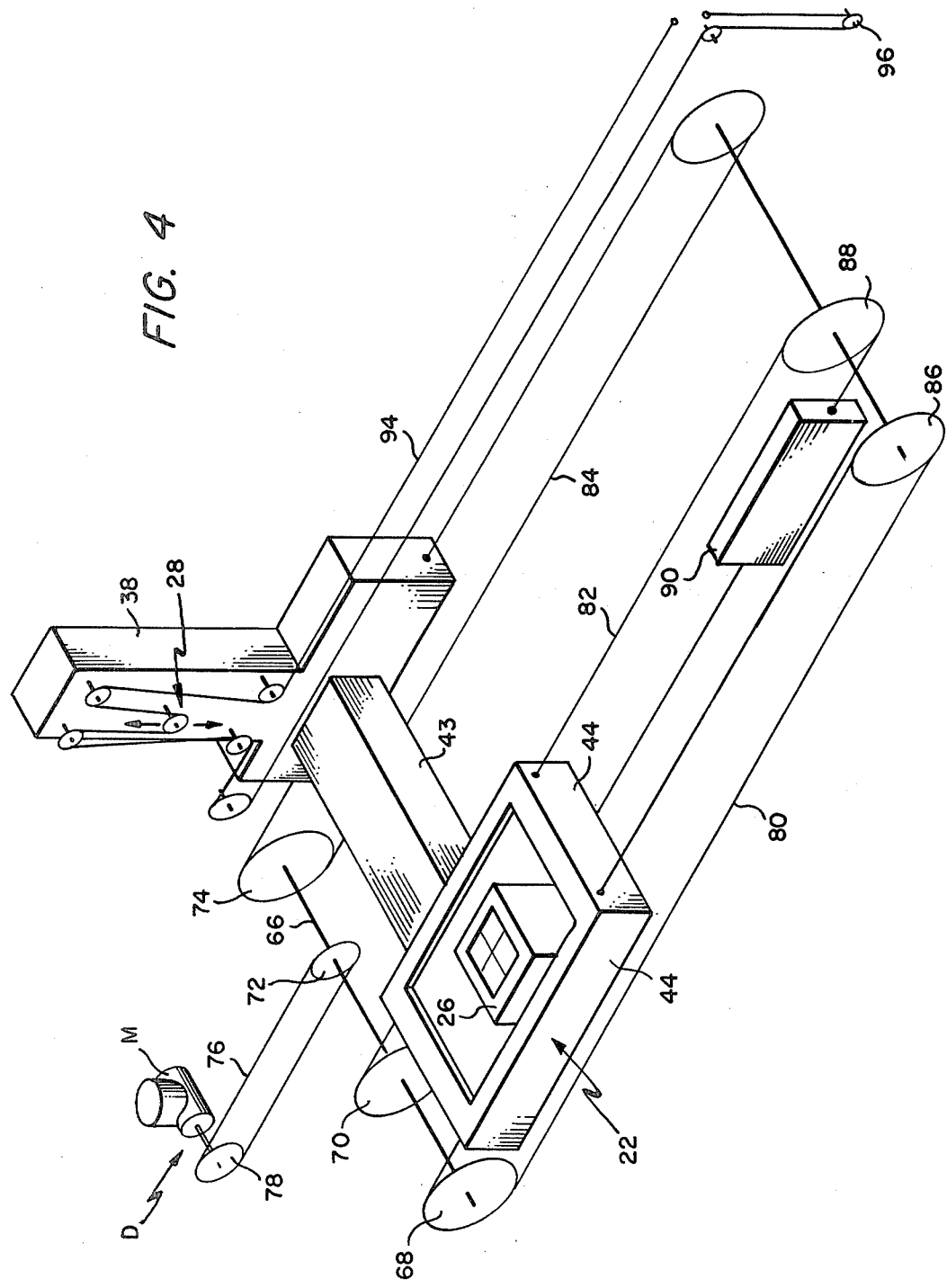
FIG. 4 is a diagram of the longitudinal adjustment mechanisms.

Referring to FIG. 4, it will be seen that longitudinal movements of the receptor and source assemblies are accomplished by pulleys and cables under control of the motor M. A drive or line shaft 66 carries a number of pulleys 68, 70, 72 and 74, simultaneous rotation of which is effected by rotation of the shaft 66. Shaft 66 is rotated by a cable 76 which is extended over pulley 72 and another pulley 78 which is driven by motor M, this constituting the drive unit D.

Since longitudinal movements of both the receptor assembly 28 and source assembly 22 simultaneously is desired, cables 80, 82 and 84 are wound upon respective pulleys 68, 70 and 74. Cable 80 is extended over another pulley 86 and its ends are attached to opposite sides of the source assembly frame 44. Thus, longitudinal movement of the source assembly 22 is effected upon operation of motor M.

The second cable 82 is similarly attached to the frame 44 and is wound upon pulley 70 and an additional pulley 88 to supplement the function of cable 80. Cable 82 is shown as carrying a counterweight 90 for counterbalancing the weights of the assemblies when the table is tilted to an upright or perpendicular position.

As described, the receptor assembly 28 is attached to the source assembly 22. In FIG. 4 the receptor assembly 28 is diagrammatically illustrated by a vertically movable point or circle on tower 38 which is connected to frame 44 by bar 43. The cable 84 is attached at its ends to opposite sides of the tower 38 and is wound upon the pulley 74 and another pulley 92 to effect movement of the tower 38 and consequently of the receptor assembly 28 when the motor M is operated.

The vertical adjustment of the receptor assembly 28 is accomplished manually through a cable 94 and additional pulleys, as shown, together with a counterweight 96.

In accordance with the invention, a handle 100 is shown secured by a shaft to the receptor assembly 28, the handle and shaft being adapted to slide in a direction longitudinally of the handle. A switch 102 is positioned on the receptor assembly and is activated by sliding movement of the handle. As will be seen in FIG. 5, the switch 102 forms a part of an electrical circuit for activating the motor M and the clutch 104 for operating the drive unit D in response to a movement of the handle 100. The driving force exerted by the motor M is insufficient to overcome the frictional forces of the drive unit D plus the frictional forces between the assemblies and the frame members 40 and 58 supporting the assemblies. The C- frame with the receptor assembly 28 and the source assembly 22 is set in motion under the combined forces of an operator pushing on the handle 100 plus the force exerted by the motor M. When the operator pushes the handle 100 in one direction, the handle 28 activates the switch 102 to provide movement of the C-frame. Similarly, when the operator pushes the handle 28 in the opposite direction the handle 100 operates the switch 102 to activate the motor M for driving the C-frame in the opposite direction. In this way, the motor M acts as a power assist for the operator while retaining a feel for the movement of the structure in the hand of the operator since the assemblies do not move until the operator has exerted sufficient force on the handle 100 to overcome the aforementioned frictional forces.

Figure 5:
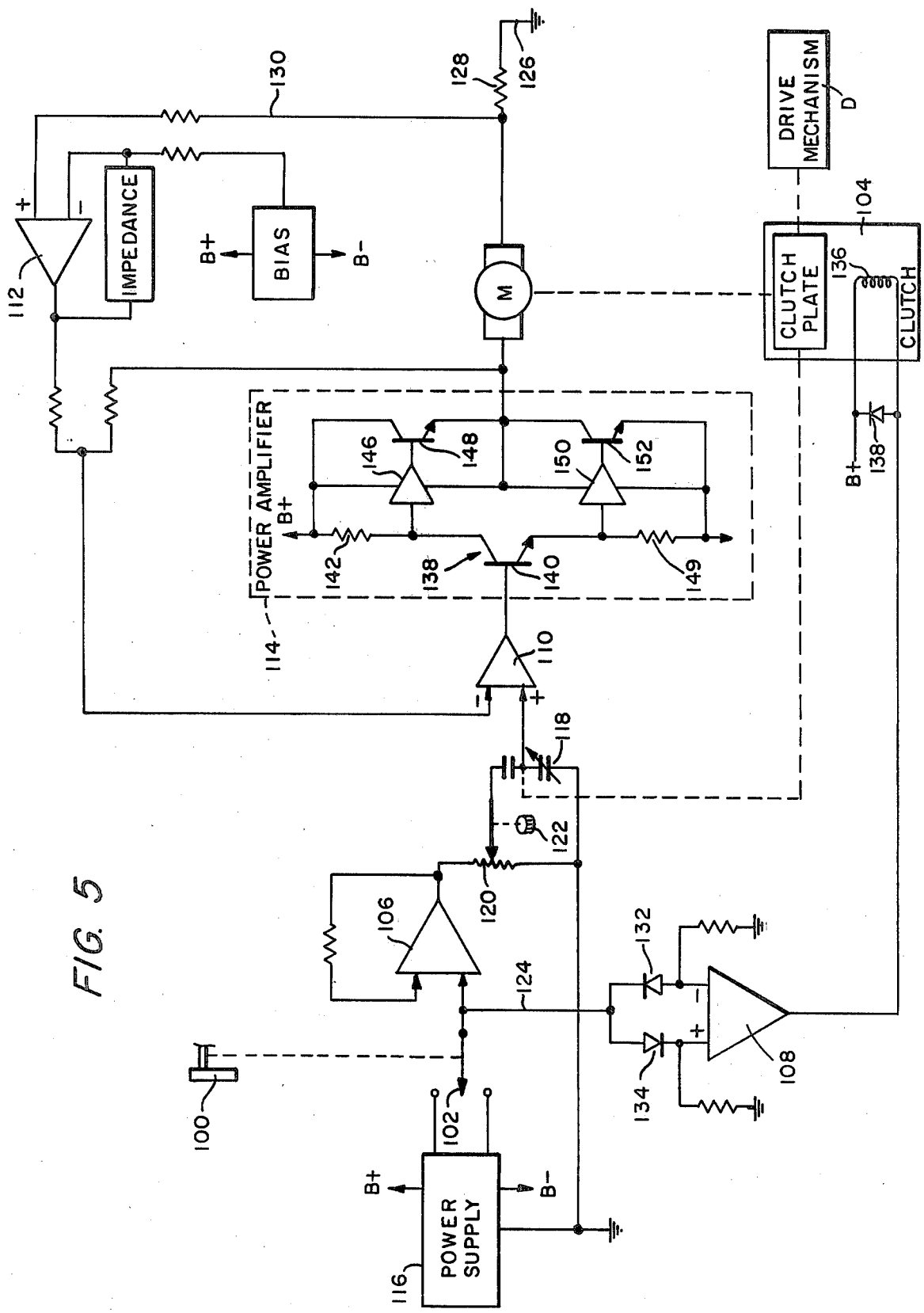
FIG. 5 is a schematic diagram of the electrical circuit which controls the movements of the assemblies.

Referring now to FIG. 5, there is shown a schematic diagram of an electrical circuit for controlling the motor M and the coupling of the circuit to the switch 102, the motor M and the clutch 104. Mechanical connections between the motor M, the clutch 104 and the drive unit D are indicated by dashed lines in FIG. 2. Similarly, the mechanical connection between the handle 100 and the switch 102 is indicated by a dashed line. The circuit comprises four amplifiers 106, 108, 110, and 112 which are in the well known form of operational amplifiers, a power amplifier 114, a power supply 116, a relay 118 which is mechanically coupled to the clutch 104, and a potentiometer 120 which is operated by a knob 122 for selecting the magnitude of the torque to be applied by the motor M to the drive unit D.

In operation, the power supply 116 provides four polarities of voltage indicated in the Figure by the legends B+, B−, +V and −V. The voltages +V and −V are coupled respectively by the two terminals of the switch 102 to line 124 whereby the switch 102 alternately selects either +V for driving the C− frame in one direction, or −V for driving the C− frame in the other direction, or, alternatively, the switch 102 has its movable contact in the center position whereby both of the two voltages are decoupled from the line 124 to provide for deactivation of the motor M and the clutch 104. Assuming that the switch 102 is coupling either the voltage +V or the voltage −V to line 124, the voltage on line 124 is of sufficient magnitude to saturate the amplifier 106 to provide fixed magnitudes of voltage, either +V or −V, across the terminals of the potentiometer 120. Thereby, upon adjustment of the torque knob 122 to produce a desired excitation of the motor M, that excitation remains fixed to provide a fixed amount of power assist to the operator. The output terminal of the potentiometer 120 is coupled via the normally open contact of the relay 118 to the amplifier 110. The normally open contact of the relay 118 blocks the passaage of an electrical signal from the potentiometer 120 to the amplifier 110 until after the clutch 104 has become activated to couple the motor M to the drive unit D. Upon activation of the clutch 104, the relay contact then closes to couple the electrical signal from the output terminal of the potentiometer 120 to the amplifier 110. The signal is then amplified by the amplifier 110, further amplified by the power amplifier 114, and then applied to one terminal of the motor M. The other terminal of the motor M is coupled to ground 126 by a resistor 128 of relatively small value, typically 0.1 ohm, for a measurement of the current flowing through the motor M.

The motor M comprises a permanent magnet, and, as is well known, such a motor produces a torque proportional to the current flowing through the motor, that current being measured by a voltage proportional thereto which appears across the resistor 128. The voltage appearing across the resistor 128 is applied as a feedback signal via line 130 and the amplifier 112 to the negative input terminal of the amlifier 110 to insure a linear relationship between the voltage on line 130 and the voltage at the output terminal of the potentiometer 120. Since, as noted hereinbefore, the voltage on line 130 is proportional to the motor current, the motor current is therefore proportional to the voltage selected by the potentiometer 120 and, accordingly, the torque produced by the motor has a predetermined value in accordance with the setting of the torque knob 122.

With reference to the coupling of the line 124 to the amplifier 108, a pair of diodes 132-134 are connected between the line 124 and the input terminals of the amplifier 108, the cathode of the diode 132 being coupled to the line 124 while the anode of the diode 132 is coupled to the negative, or inverting, terminal of the amplifier 108, and the anode of the diode 134 is coupled to the line 124 and the cathode of the diode 134 is connected to the positive terminal of the amplifier 108. Thereby, upon the application of either a voltage of +V or of −V on the line 124, the output terminal of the amplifier 108 produces a voltage of positive polarity to activate a coil 136 within the clutch 104. A diode 138, across the terminals of the coil 136, facilitates discharge of the current in the coil 136 upon deactivation of the clutch 104.

The power amplifier 114 is seen to comprise a phase splitter 138 which includes a transistor 140 coupled via resistors 142 and 144 between the B+ and the B= voltage terminals. The collector terminal of the transistor 140 is coupled via an amplifier 146 to the base terminal of a transistor 148 for applying a voltage of a first plurality to the terminal of the motor M. The emitter terminal of the transistor 140 is coupled via an amplifier 150 to the base terminal of a transistor 152 for application of a voltage of the opposite plurality to the terminal of the motor M. Thus, the amplifier 114 is capable of providing a power amplification to a signal of positive or negative plurality for driving the motor M in either a clockwise or counterclockwise direction for driving the C- frame in the selected direction.

From the foregoing it will be apparent that the described invention will enable a heavy unit of components to be moved longitudinally of a fluoroscopic table by the use of a motor which will perform a major portion of the power while manual power may be used to supplement the motor power. The manual power will be of only slight degree and may be selected to provide individual feel for the movements of the apparatus.

It will be apparent that various modifications and changes in the structures shown and described and in their operation may be made by those skilled in the art without departing from the spirit of the invention as expressed in the accompanying claims. Therefore all matter shown and described is to be interpreted as illustrative and not in a limiting sense.

What is claimed is:

1. A fluoroscopic table comprising a base, a patient-supporting top on the base, a radiation source assembly within the base for generating a beam of X-rays, a receptor assembly spaced from the base in position to receive said X-ray beam, electrical power means for moving said source and receptor assemblies simultaneously longitudinally of the table, said power means comprising a motor, and an electrical power circuit which provides controlled current flow to the motor for producing a constant output torque at the motor of a value nearly that which will move said assemblies, and means for applying manual force to the assemblies to supplement said power means.

2. A fluoroscopic table as set forth in claim 1 wherein said motor is a series wound DC motor, and said torque is adjustable.

3. A fluoroscopic table comprising a base, a patient-supporting top on the base, a radiation source assembly within the base for generating a beam of X-rays, a receptor assembly spaced from the base in position to receive said X-ray beam, electrical power means for moving said source and receptor assemblies simultaneously longitudinally of the table, said power means comprising a motor, and an electrical power circuit which provides constant current flow to the motor whereby the motor voltage will vary inversely with its speed and produce a constant output torque, and means for applying manual force to the assemblies to supplement said power means.

4. A fluoroscopic table as set forth in claim 3 wherein means is provided for regulating said torque.

5. A fluoroscopic table comprising a base, a radiation source assembly within said base for generating a beam of X-rays, a receptor assembly spaced from said base in position to receive said X-ray beam, a frame interconnecting said source and receptor assemblies, drive means for moving said assemblies comprising a line shaft, a motor for driving said shaft, a first set of pulleys on said shaft for rotation therewith, pulleys spaced from the shaft, and cables connected at opposite ends to opposite sides of said assemblies and wound on said pulleys for simultaneously moving said assemblies in a common direction longitudinally of the table, and electrical power means which provides controlled current flow to the motor for producing a constant output torque at the motor of a value nearly sufficient to operate said drive means, and means for applying manual force to the assemblies to supplement said power means.

6. A fluoroscopic table as set forth in claim 5 wherein means is provided for regulating said torque.

7. A fluoroscopic table comprising a base, a patient-supporting top on the base, and X-ray source assembly within the base for generating a beam of X-rays and directing said beam through said top, a receptor assembly spaced from the base in position to receive said X-ray beam, said source and receptor assemblies being interconnected for simultaneous movement as a unit, drive means for moving said assemblies including a motor, movable handle means mounted on said receptor assembly for manually moving said assemblies, switch means engageable by said handle means for initiating operation of said motor, and electrical circuit means connected to said switch and motor for providing sufficient power to said motor when the handle means is moved to produce a constant output torque at the motor of a value somewhat less than that necessary to move said assemblies.

8. A fluoroscopic table as set forth in claim 7 wherein said torque is of a predetermined value equal to a major portion of the torque value required to move the assemblies whereby a small controlled manual effort supplemental to said predetermined value will effect movement of the assemblies.

9. A fluoroscopic table as set forth in claim 7 wherein said handle means is movable in two selected directions, and said switch means comprises two elements respectively operable when the handle means is moved in opposite directions to control operation of the motor to move the assemblies in a selected direction longitudinally of the table.

10. A fluoroscopic table as set forth in claim 7 wherein said handle means is movable in two selected directions, and said switch means comprises two separate spaced contacts connected respectively through separate circuitry to the motor for driving the motor in respective opposite directions, said handle closing a selected switch contact corresponding to its direction of movement whereby torque will be created in the motor of a value nearly sufficient to move the assemblies and such that movement of the assemblies will occur when said torque value is supplemented by minor manual effort upon the handle means.

* * * * *

UNITED STATES PATENT OFFICE
CERTIFICATE OF CORRECTION

Patent No. 4,208,586           Dated June 17, 1980

Inventor(s) James R. Craig and Steven F. Nerge

It is certified that error appears in the above-identified patent and that said Letters Patent are hereby corrected as shown below:

On cover sheet, Item [73] Assignee:, change "Raytheon Company, Lexington, Mass." to -- The Machlett Laboratories, Incorporated, Springdale, Connecticut --.

Signed and Sealed this

Fourteenth Day of October 1980

[SEAL]

Attest:

SIDNEY A. DIAMOND

Attesting Officer    Commissioner of Patents and Trademarks